United States Patent [19]

Seale

[11] Patent Number: 5,533,381
[45] Date of Patent: Jul. 9, 1996

[54] CONVERSION OF LIQUID VOLUME, DENSITY, AND VISCOSITY TO FREQUENCY SIGNALS

[76] Inventor: Joseph B. Seale, 36 Ledge La., Gorham, Me. 04038-1208

[21] Appl. No.: 258,198

[22] Filed: Jun. 10, 1994

[51] Int. Cl.$^6$ .......................... G01N 9/00; G01N 11/16; G01F 1/76
[52] U.S. Cl. ...................... 73/19.03; 73/32 A; 73/54.25; 73/54.26; 73/861.18
[58] Field of Search .................... 73/19.03, 19.1, 73/54.41, 54.25, 54.26, 61.45, 61.49, 61.79, 64.53, 32 A, 579, 702, 861.18

[56] References Cited

U.S. PATENT DOCUMENTS

| | | | |
|---|---|---|---|
| 2,711,646 | 6/1955 | Mendousse | 73/64.53 |
| 3,425,281 | 2/1964 | Barz | 73/702 |
| 3,620,083 | 11/1971 | Dimeff et al. | 73/702 |
| 4,098,133 | 7/1978 | Frischeet et al. | 73/702 |
| 4,297,872 | 11/1981 | Ikeda et al. | 73/32 A |
| 4,479,070 | 10/1984 | Frische et al. | 310/338 |
| 4,572,003 | 2/1986 | Fritz | 73/861.18 |
| 4,644,803 | 2/1987 | Ward | 73/862.58 |
| 4,721,874 | 1/1988 | Emmert | 73/54.41 |
| 4,783,987 | 11/1988 | Hager et al. | 73/32 A |
| 4,872,335 | 10/1989 | Tsuruoka et al. | 73/32 A X |
| 4,996,656 | 2/1991 | Hedrick | 73/32 A X |
| 5,123,285 | 6/1992 | Lew | 73/861.20 |
| 5,323,638 | 6/1994 | Langdon | 73/32 A |

Primary Examiner—Michael J. Brock
Attorney, Agent, or Firm—Chris A. Caseiro; Thomas L. Bohan

[57] ABSTRACT

Volume of a working liquid in a sensing chamber is measured via a first mechanical resonance frequency. A second resonance may be measured to discriminate interacting volume and density effects, yielding corrected volume, density, and liquid mass. A probability of bubbles present in the liquid is indicated by an abnormal combination of first and second resonances. Determination of a frequency and an associated phase angle near a resonance may be used to discriminate interacting volume and viscosity effects, yielding corrected volume and viscosity. One boundary of the sensing chamber is a deformable plate, which may be rippled to increase the range of linear volumetric compliance. A second boundary paralleling the plate captures a thin variable-thickness fluid layer. Vibrations in the plate cause amplified fluid vibrations parallel to the plate surface, causing a high, thickness-sensitive fluid inertia that lowers plate resonance frequencies in a volume-sensitive manner. A transducer coupled to the resonant plate transforms the mechanical resonances into electrical resonances, which are electronically transformed into frequency readings. A first elastic barrier may contain liquid in a separable disposable container and conform directly to the mated vibrating plate, or to a second elastic barrier, which may be used, first, to retain working liquid on the sensing chamber side, and second, to couple volume changes via the working liquid into the sensing chamber from a second, measured liquid on the disposable side.

47 Claims, 5 Drawing Sheets

I → F
V ← Ẋ

V → F
Q ← X

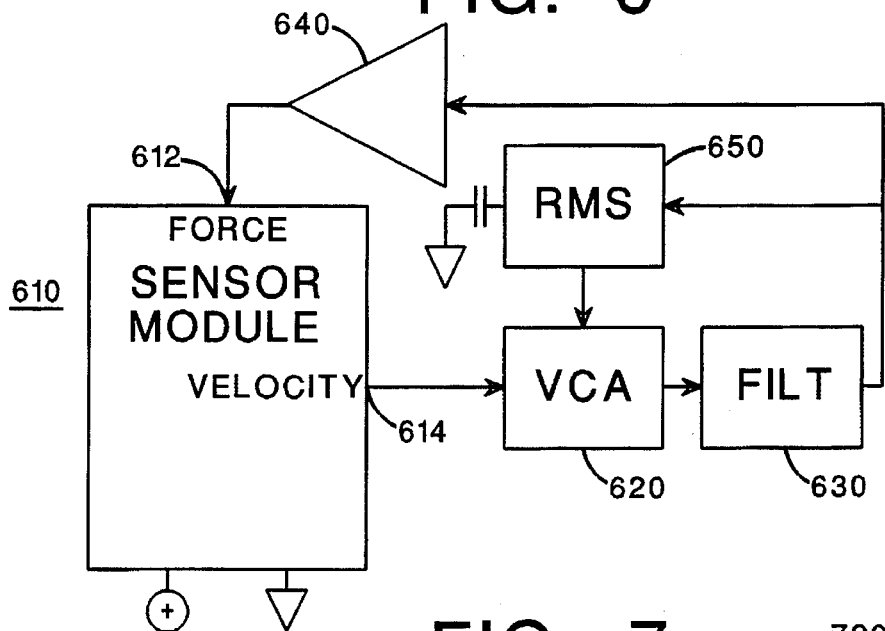
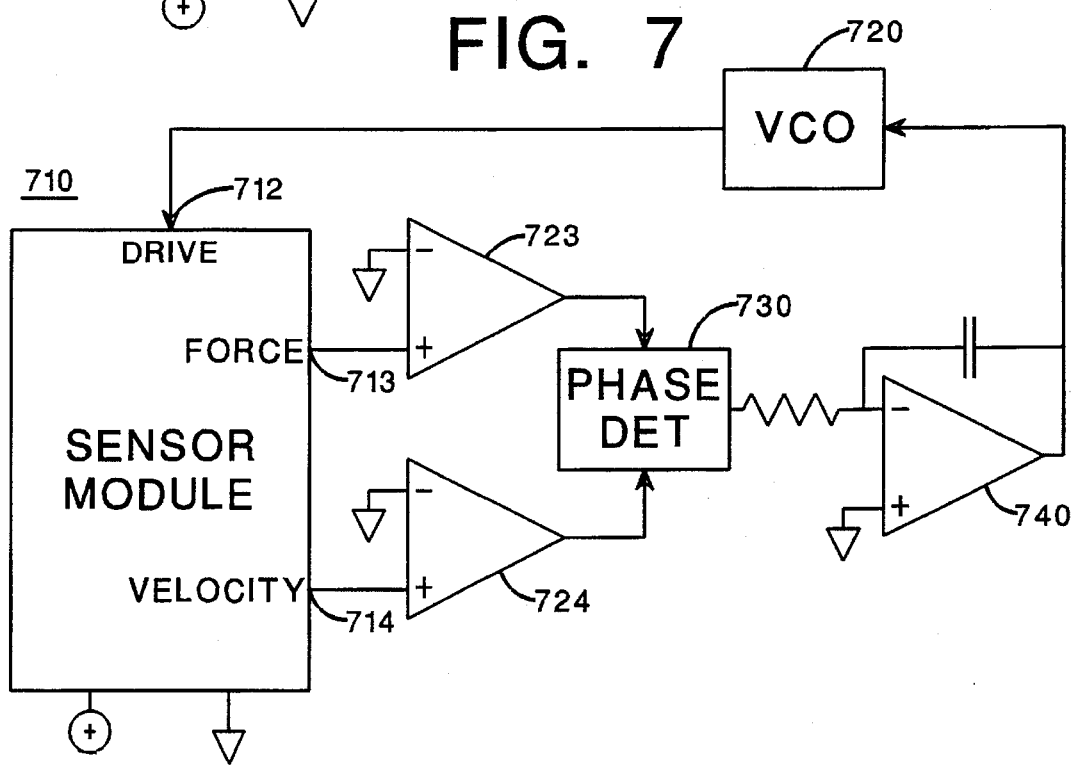

CONVERSION OF LIQUID VOLUME, DENSITY, AND VISCOSITY TO FREQUENCY SIGNALS

CROSS-REFERENCE TO RELATED APPLICATION

This invention is related to the Joseph B. Seale U.S. patent application Ser. No. 08/258,327 filed concurrently for A RESONANT SYSTEM TO PUMP LIQUIDS, MEASURE VOLUME, AND DETECT BUBBLES.

BACKGROUND OF THE INVENTION

1. Field of the Invention

The present invention relates to a device and a method for measuring the volume of a transferable liquid, the density of the liquid, and/or the viscosity of the liquid and converting any one or all of those characteristics into a corresponding frequency signal. More particularly, the present invention relates to a system for applying a signal to a device in contact with the liquid to be characterized, obtaining the resonant response of the device, and transforming that response into a frequency signal that can be utilized to characterize the liquid with great accuracy.

2. Description of the Prior Art

There is a large patent and engineering literature concerning capacitance strain gauges for use in fluid measurements, typically adapted to pressure measurement at minimized sensor volume displacement. Some (e.g. Hewlett Packard Model 1290 Series Quartz Transducer) have been adapted to medical fluid control, sensing pressure across a membrane and obtaining a small deflection of a strain gauge surface that mates with the membrane. In many applications, e.g., with medical liquids and in analytical chemistry and manufacture, accurate knowledge of volume is of primary importance, while only an approximate knowledge of pressure is needed for status monitoring (e.g., to determine whether pressure in the patient IV line is indicative of normal unobstructed flow). In common engineering practice, knowledge of volume is most often obtained by positive-displacement pumping or dispensing, rather than by volume displacement sensing. An inherent disadvantage to measurement by mechanical positive-displacement fluid pumping or dispensing is that the inherent mechanical limitations of the fluid delivery system—stick-slip-stick instability in sliding fluid seals, hysteresis in elastomer fluid seals, backlash in gears and cams—become inherited limitations of the implicit fluid measurement. For precision quantitative measurements, fluid mass (weight) is often used rather than volume, but mass measurement on a scale or balance is vibration-sensitive and requires taking a fluid into an isolated environment, free of tugging tubes, etc. Reading volume from a fluid meniscus has its own limitations in both accuracy and adaptability to automation.

It would be useful to have a strain gauge transducer whose volume compliance is sufficiently large and linear to permit its use for direct measurement of volume, with a perhaps less-accurately controlled pressure calibration based on the pressure/volume characteristic of the device. While many strain gauge pressure transducers are in fact small-volume transducers calibrated in relation to their pressure/volume slope as pressure transducers, these designs have not been adapted to sufficiently large displacements and small pressure/volume slopes to make them useful for most direct volume measurements.

In designing for larger volume displacements, a problem arises with deflection in flat plates. When a plate is nearly flat, its elastic response is approximately linear and determined by the stiffness of the plate in bending, but as larger volumes cause significant curvature in the plate, the combination of curvature and tension in the surface gives rise to a steeply-rising pressure/volume curve, approximating a cube-law term adding significantly to the linear response term even at comparatively small deflections. While a certain amount of consistent, well-characterized nonlinearity is usually acceptable in a measurement system that includes a microprocessor capable of applying a non-linear calibration curve to incoming data, the extreme stiffening of a plate as it becomes curved usually generates too much back pressure at high displacements. Driven to excessive deflection, initially flat plates rupture.

A problem associated with capacitance strain gauges at large deflection is that the capacitance magnitude becomes too small for accurate measurement when the plates are pushed too far apart. Another problem with capacitance strain gauges is an inappropriate scaling of relative sensitivity. In the Hewlett Packard pressure sensor, for example, increasing pressure from a disposable membrane on an external surface reduces the internal capacitance gap, causing a steepening capacitance change at high pressure. This rising sensitivity curve is opposite to what is needed in many applications: a high sensitivity to volume and pressure changes at low pressures, and a declining sensitivity at higher pressures, so that fractional errors remain roughly constant.

The utility of a precision volume sensor with a comparatively high, comparatively linear, and consistently characterized volume/pressure compliance, is apparent from the above discussion and is readily recognized by engineers who deal with the tradeoffs in volume measurement. The practical utility of a frequency output, easily quantified by a frequency or period counter at a microprocessor interface, exceeds the utility of a system requiring an analog/digital conversion in many contexts.

OBJECTS AND IMPROVEMENTS OF THE PRESENT INVENTION

An object of the present invention is to provide a "Direct Volume Converter" (DVC) device: a direct conversion of volume displacement to frequency with low hysteresis and low drift with time, temperature, and barometer. The displacement is usually across at least one, and typically two, membranes, so that the liquid whose volume is being measured may be contained and isolated in a cassette, away from the reusable DVC apparatus. Since the detailed shape of a bulging membrane or elastomer interface may vary from unit to unit at the same total volume displacement, an object is to make the volume determination insensitive to shape variations in the interface membrane that do not represent a change in volume. A further object is to achieve reproducibility and comparative linearity in the pressure/volume curve of the device. A further object is to achieve a wide dynamic range with a maximum sensitivity at the low-pressure low-displacement end of the response curve. Still a further object is to infer the density and viscosity of the fluid that interacts with the DVC, through frequency response interpretation alone. These and other objects and advantages of the present invention will be apparent in the following specification and claims.

SUMMARY OF THE INVENTION

A volume displacement in a working liquid is measured via mechanical resonance frequency with inherently low hysteresis and drift with time, temperature, and barometer. An amount of working liquid equal to the volume displacement-to-be-measured travels into (or out of) a sensing chamber that is kept free of uncontrolled quantities of compressible gas (typically being gas free). One boundary of the chamber is a deformable plate, opposite which a second surface confines a variable-thickness fluid layer. Vibrations in the plate normal to its own surface cause amplified fluid vibrations parallel to the plate surface in the captured fluid layer. Volume-displacement-driven thickness variations in the layer alter the fluid inertia entrained by plate vibrations, thus altering the mechanical resonance frequency of the plate to yield a volume-calibratable frequency signal. The reciprocal square of resonance frequency varies approximately in linear proportion to the sum of a constant plus the reciprocal of net fluid volume captured beneath the resonant plate. The additive constant is related to the fixed mass of the plate and coupled electromechanical transducer.

An electromechanical transducer couples to the resonant plate and transforms the mechanical resonance into an electrical resonance that is sensed, yielding an electrical output signal calibratable to volume. Transduction modalities include electromagnetic (e.g., a voice coil driver), electrostatic (e.g., as in a capacitance microphone), and piezoelectric (e.g., as in a bending-mode buzzer). Motion sensing in the transducer may be accomplished by direct measurement of the impedance of the transducer (e.g., putting a voice coil or piezo element in a balanced bridge circuit), or by use of a second sensing transducer, often conveniently a part of the driver transducer (e.g., using a sense winding coaxial with a driving voice coil, or using a sense area electrically isolated from the driver area on a single piezoelectric bender element). For sensing alone, resistive-strain-gauge sensors may be used to measure AC plate bending in a resonant measurement. Any fluid-pressure sensor having adequate bandwidth can be used to sense AC pressure response below the plate, which in combination with a plate-driver transducer can be used to sense plate resonance.

The deformable vibration plate in a preferred embodiment is made from a single flat piece of spring-metal sheet, die-formed to have a curved perimeter ridge for more linear volume/pressure compliance and higher total displacement capacity than would be practical with an unformed sheet. The center region of the sheet, defining one of the boundaries of the captured vibrating fluid layer, is kept flat, for consistency of vibration characteristics and insensitivity to variability of the forming operation. In the perimeter region of a sheet, the fluid layer is much thicker than near the center, so that sensitivity of vibration frequency to fluid layer thickness is much reduced. By design, inconsistencies in forming of the perimeter metal are caused to have a relatively small effect on the lowest-frequency vibration modes used to measure volume.

It is common to isolate the working liquid from a deliverable liquid whose displacement is measured via a deformable elastic barrier, e.g., in a cassette. In a preferred embodiment, a first elastic barrier containing deliverable liquid in a cassette mates with a second elastic barrier containing working liquid in a sensor assembly, with displacement from cassette to sensor across the mated barriers driving working liquid into the fluid layer against the plate in the sensing chamber. In a second embodiment, the deliverable liquid functions as the working liquid, being vibrated directly by the plate, even though a membrane coupling to the plate surface may still be used to contain the fluid in a cassette. Interpreting the frequencies obtained from more than one resonant mode and from a given resonance perturbed by differing phase-shifts in the excitation loop, the density, viscosity, and volume of the measured liquid are determined by simultaneous mathematical solution. In some applications, determination of density and viscosity may prove of equal or greater importance than volume displacement measurement. Even in the preferred embodiment, where density and viscosity of the deliverable liquid are not measured, this multi-frequency fluid property analysis minimizes temperature sensitivity of the volume result and also leads to bubble detection.

To obtain density self-calibration, note that all radially-symmetric modes of plate vibration are affected by coupled effective fluid mass, which varies in proportion to fluid density and inversely in proportion to "effective thickness" of the fluid layer as a function of radius. "Effective thickness" is taken to mean actual thickness minus top- and bottom-surface boundary layer thicknesses, as is explained in more detail later. It is seen that an increase in volume beneath the plate, with accompanying increase in fluid layer thickness, could be confused with the effect of increased "specific-volume" i.e. increased "reciprocal-fluid-density" since both effects lower plate-coupled fluid inertia and therefore raise the various resonance frequencies. To resolve separately the effects of volume change from specific-volume change, one must take into account that a change in volume does not change fluid layer thickness by the same fractional amount at all radii, for two reasons: first, because the vibration plate changes in shape as it deforms with volume change, and second, because the fluid layer thickness may be made non-uniform by design, in order to emphasize differences in how fluid volume change alters different resonant modes. Hence, the shape of the radial distribution of fluid mass impedance affecting plate vibration is altered by volume change, whereas specific-volume change alters only the average value, leaving the shape of the radial distribution unaltered. It is this shape alteration that results in different effects on different vibration mode shapes. A design goal for two-mode resolution of volume and density is to obtain two measurable vibration-mode frequencies from which can be resolved, by simultaneous solution from calibration formulas, separate values for volume and density. To avoid singular or near-singular simultaneous solution, the geometry of the measurement system must assure that one mode frequency is relatively more sensitive to volume change than another, as compared against sensitivity to specific-volume change as a baseline. Volume and density computations depend on "effective thickness" of the fluid layer, which is altered by viscosity-sensitive boundary layer effects, as now described.

To obtain viscosity self-calibration, viscosity determines the resonant damping factor, which in turn is almost linearly related to the fraction of fluid layer thickness occupied by the vibrational boundary layer. The damping factor controls the sharpness of the resonance, which is inferred from frequency measurement alone by perturbing the phase angles between applied vibrating force and responsive vibrational velocity, determining how the measured frequency changes in response to these phase perturbations. Vibrational boundary layer thickness perturbs the volume-indicating resonant frequency, but the needed frequency correction is closely related to the damping factor determined by measurement.

The most accurate analysis uses a minimum of three measured frequencies, a "fundamental", a "phase-perturbed fundamental", and a "harmonic", to use in simultaneous solution for volume, density, and viscosity, accounting for all the physical interactions.

It will be seen that temperature dependence of viscosity is readily compensated for without temperature measurement, relying instead on the more direct linkage between viscosity, damping factor, and volume correction.

BRIEF DESCRIPTION OF THE DRAWINGS

FIG. 6 illustrates a regenerative automatic-gain-control oscillator circuit to drive a transducer in phase with its output velocity-sense signal.

FIG. 7 illustrates schematically a phase-lock-loop oscillator circuit to drive a transducer so that sensed force and sensed velocity are in phase.

DESCRIPTION OF PREFERRED EMBODIMENTS OF THE INVENTION

Figure 1A:
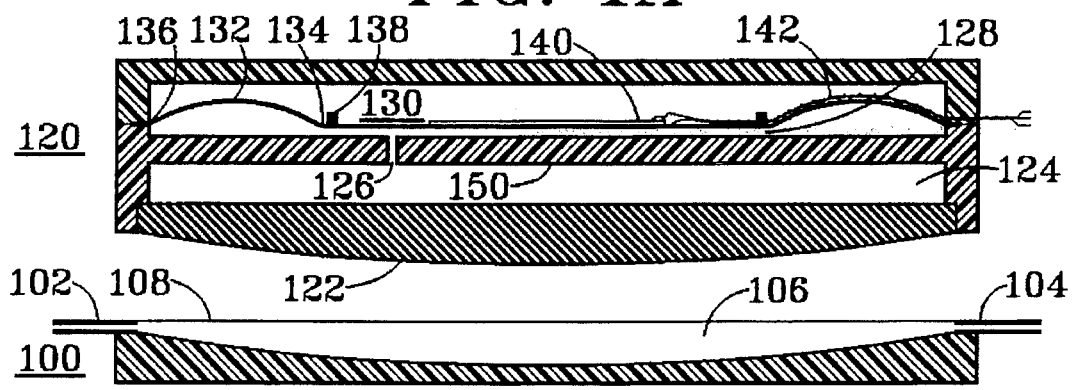
FIG. 1A illustrates in section view a direct volume conversion sensor directly above a disposable fluid cassette, the sensor producing a volume displacement sensing vibration frequency utilizing a piezoelectric ceramic transducer disk laminated to a formed metal resonator disk.
Figure 1B:
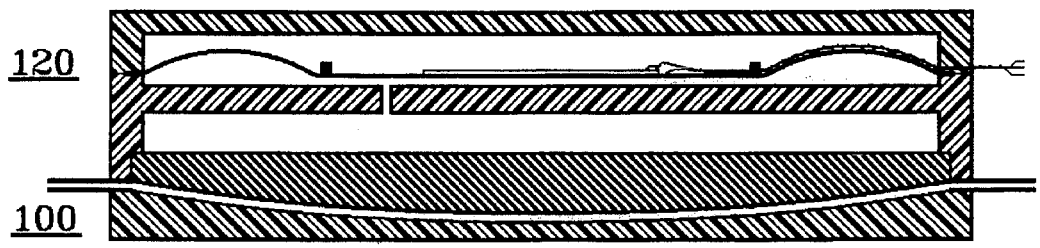
FIG. 1B illustrates coupling of the sensor and cassette components of FIG. 1A.
Figure 1C:
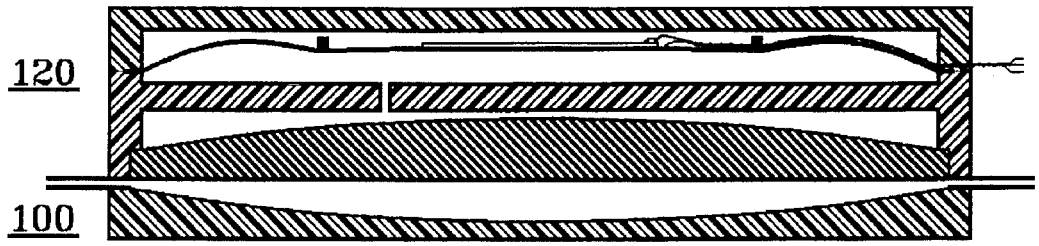
FIG. 1C illustrates upward displacements of the disk and fluid barrier components of FIG. 1B when a fluid volume enters the cassette.

Referring first to FIG. 1A, sensor module 120 is shown above cassette interface 100. The cassette interface includes fluid inlet 102, outlet 104, fluid reservoir 106, and elastic interface membrane 108. Mating with interface 108 on the sensor module side is elastic plug 122, which is thick enough to retain a well defined surface shape and made of an elastomer material so that the plug deforms easily to permit volume displacement. When the sensor module and cassette are separate, the external surface of 122 is convex, so that it will make contact with membrane 108 at a center footprint area that will spread as the cassette and sensor module are clamped together, avoiding captured air in the interface. FIG. 1B illustrates the sensor module and cassette in clamped contact, with the elastomer material pressing in on the cassette membrane and displacing fluid out of the fluid reservoir. In FIG. 1C, the original fluid volume has been restored to reservoir 106, pushing up and flattening the lower surface of plug 122. This action in turn displaces working fluid out of sensor cavity 124 through orifice 126 in rigid barrier 150 into fluid layer 128, between rigid top surface of 150 and the deformed surface of resonator plate 130, which is pushed upward in FIG. 1C as compared to its resting shape of FIGS. 1A and 1B. Plate 130 is fabricated by die-forming a thin (e.g. 0.008 inches) sheet of spring metal (e.g. beryllium copper alloy) so that its center area is flat and its perimeter area includes at least one circular ridge or bump—a single ridge being demonstrated to perform quite well in this preferred embodiment. The top of the ridge is noted at 132 in FIG. 1A, and again at 132 in the plan view of the formed plate 130 provided by FIG. 2, with the inner boundary of the ridge shown at 134 and the outer boundary at 136 in both FIGS. 1A and 2. These figures also show balance ring 138, located on the flat plate surface just inside the inner bump boundary at 134. Ring 138 corrects the mass distribution of the plate 130 to minimize vibrational coupling to the outside world, as discussed subsequently in regard to specific details of that component of the present invention.

Vibration modes in plate 130 are determined by the elasticity of the plate and by inertia especially from two sources: the mass of the plate itself, and the effective mass of fluid captured in fluid layer 128. When the plate surface vibrates in a nearly vertical motion, i.e., axially and nearly perpendicular to the thin surface, then the fluid in 128 is forced to move nearly radially as it is squeezed away from descending portions of the plate surface and drawn beneath ascending portions of the plate surface. When the fluid layer is very thin compared to the plate radius, then the radial fluid motions are much larger that the axial plate motions, with the result that fluid velocities exceed plate velocities and kinetic energy in the fluid exceeds kinetic energy in the plate, commonly by a margin of 10-to-1 or more. To say that fluid kinetic energy exceeds plate kinetic energy is to say that the effective inertia contribution from fluid motion exceeds the contribution from plate metal. When additional fluid is displaced into layer 128, as illustrated in FIG. 1C, then the fluid layer becomes thicker and the fluid is not forced to travel at such high velocity compared to the plate surface. Even though the amount of fluid in motion is greater in FIG. 1C than in FIG. 1A, the total kinetic energy is less. Consider, for example, a doubling of fluid layer thickness, accompanied by a halving of radial velocity to accomplish the same radial volume displacement and accommodate a given axial plate motion. For half the fluid velocity, velocity-squared is down by a factor of four, but for twice as great a moving mass in the thickened layer. The energy product of mass times velocity-squared is thus reduced to half when fluid layer thickness is doubled. The resulting halving of fluid inertia raises the plate resonant frequency a factor slightly less than the square root of two, the reduction from the exact square root of two arising because the small fraction of moving mass attributed to plate material (as opposed to fluid) remains unchanged. One thus obtains the relation that resonant frequency varies roughly as the square root of the fluid volume captured in the thin layer under the nearly-flat middle area of the plate. In practice, frequency varies by somewhat more than the square-root of fluid-layer volume, because the upward bowing of the center-plate area, seen clearly in FIG. 1C, results in an effective stiffening of the plate material with increasing curvature. The true relationship between volume and frequency can be calibrated empirically.

Figure 2:
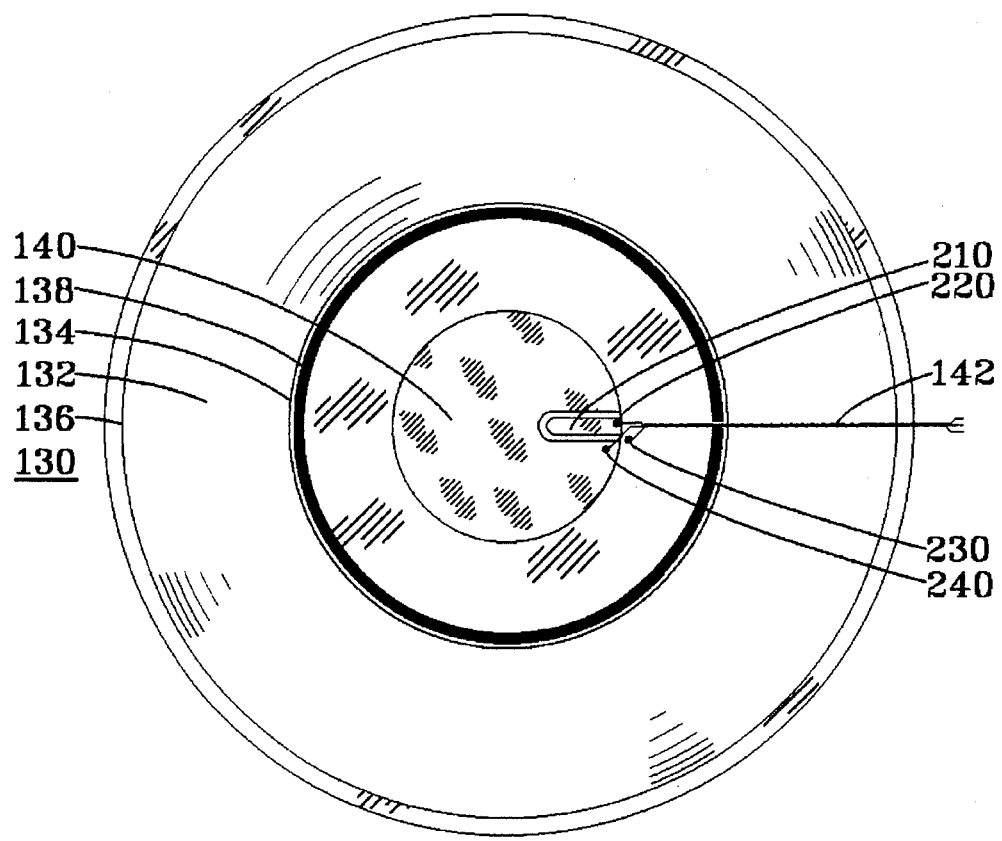
FIG. 2 illustrates in plan view the transducer and resonator disk components of FIGS. 1A, 1B, and 1C, including the drive and sense metallizations and wiring of the piezoelectric transducer.

The electromechanical interface to the plate as illustrated in FIGS. 1A, 1B, 1C, and 2 is a single thin piezoelectric ceramic disk, 140, electrically connected to the plate on the lower surface by conductive cement and metallized over most of the top surface to form a capacitor across the thickness of the disk. As is well known in the design of piezoelectric disk buzzers (as found widely in smoke alarms, telephone ringers, fasten-seatbelt beepers, etc.), an axial electric field in an axially poled thin disk causes a change in axial thickness and, according to the Poisson ratio of the ceramic, a smaller strain of the opposite polarity in the radial direction (i.e., radial contraction for axial expansion and vice versa). The radial motions induce vibratory bending in the disk 140, exciting vibration modes. Twisted wire cable 142 connects to the lower disk surface via connection to the plate at 230 and conduction via the plate and conductive epoxy to the metallization on the lower disk surface, and 142 connects to the upper plate surface via the bond at 240. A disk portion 210 of the upper disk metallization may be kept electrically isolated from the majority of the area, to serve as a sensor of plate bending. FIG. 2 illustrates a sense wire bonded to metallization area 210 at section 220, that wire becoming part of cable 142. In practice, the sense wire should not travel for a very long run in close proximity to the "live" conductor driving the disk, to minimize capacitive crosstalk.

Figure 3A:
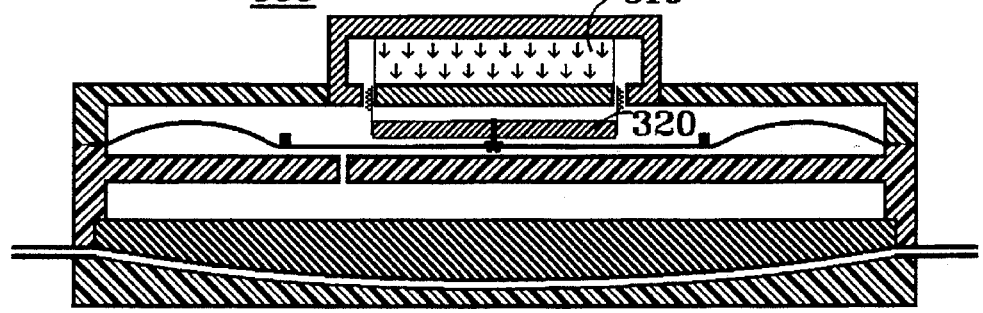
FIG. 3A illustrates a coupled sensor and cassette similar to FIG. 1B except that a voice coil driver and extra sense winding are substituted for the piezoelectric transducer disk to generate and sense vibrations.

As illustrated in FIG. 3A, a voice coil driver 300 can be substituted for the piezoelectric transducer of earlier figures. As drawn, the voice coil is mounted on a disk 320 that is attached to the center of the vibrating plate by a small (e.g., #1) screw penetrating the middle of the disk 140, held to the plate by a nut, and threaded into the low-density disk that supports the voice coil. The permanent magnet 310 in the structure, drawn in the typical shape and proportion of a rare earth magnet (as contrasted with the much larger magnet used when the material is ferrite ceramic) is indicated by a pattern of arrows illustrating the magnetic poling direction. The voice coil rests slightly below the center of the magnetic gap when the plate is undeflected, so that at a typical upward displacement due to fluid volume, the coil is centered. Well known details of voice coil driver design need not be covered here. Note that, by analogy to the sense metallization 210 of FIG. 2, a second winding may be layered coaxial with the voice coil drive winding in order to sense the voltage induced by axial coil velocity. As will be shown later, auxiliary windings or piezoelectric sense metallizations are a convenience for the engineer but not necessary to closure of the electronic oscillator loop.

Figure 3B:
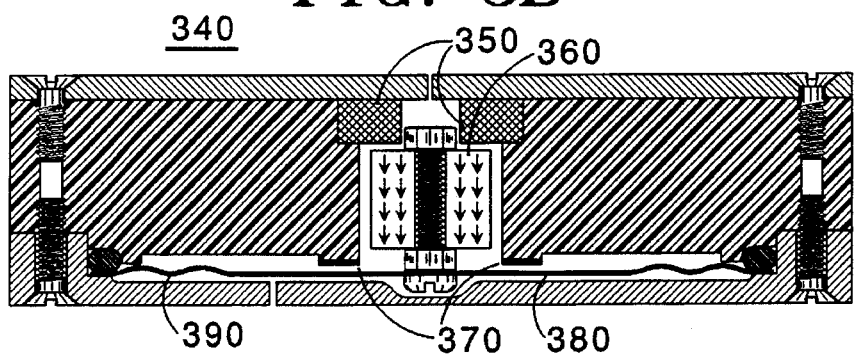
FIG. 3B illustrates a hybrid transducer combination employing a moving magnet driver or sensor and a variable capacitance sensor or driver. The outer plate region is formed with multiple annular ridges.

The drawing of assembly 340 in FIG. 3B shows a resonant plate and fluid layer structures similar to the upper halves of FIGS. 1A, 1B, 1C, and 3A, including a rigid surface like 150 with an orifice like the orifice 126 of FIG. 1A, but does not show the cassette interface 122 and assembly 100 of that drawing, below the rigid surface and orifice. The driver/sensor of FIG. 3A, with magnet 310 above the moving coil, is inverted and totally reproportioned for FIG. 3B, making a moving magnet structure comparable to that shown in FIG. 8A. Poling of magnet 360 is indicated by arrows as with the arrows on 310, but magnet 360 is mounted on a resonant disk 380 like magnet 840 on disk 830 of FIG. 8A, with disk 380 also having a similar mechanical clamping to disk 830. Coil 350 is comparable to either coil 850 or coil 860 of FIG. 8A, any one of the coils being usable for excitation or sensing. In contrast to other figures, FIG. 3B illustrates mixed electromagnetic and electrostatic transducer types, with a single magnetic coil 350 and a capacitor, formed between annular ring 370 and plate 380, being usable either for sensing or excitation. Thus, one can drive electromagnetically and sense electrostatically (as in a capacitance microphone) or drive electrostatically (as in electrostatic speakers or headphones) and sense electromagnetically. Note the variation in resonant plate design of FIG. 3B, with multi-ridge forming of plate 380 indicated at and to either side of region 390.

Figure 4:
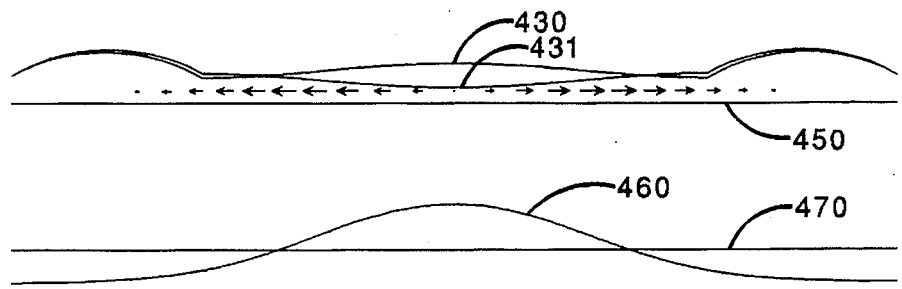
FIG. 4 illustrates in section view, to exaggerated scale, how the resonator disk of previous figures deflects axially in its lowest-frequency vibration mode, how fluid captured below the disk is displaced radially by the vibrations, and graphically how vibrational fluid pressure amplitude varies as a function of radius.

FIG. 4 illustrates the motions of the plate and fluid for a useful lowest-frequency plate vibration mode. Plate 130 is illustrated as a pair of contours, 430 and 431, where 430 illustrates upward deflection of the center and downward deflection of the perimeter, and vice versa for 431. Line 450 represents the top surface of rigid barrier 150. The horizontal (radial) arrows between 450 and 431 represent fluid acceleration, or fluid velocity, or fluid displacement, depending on the phase of the vibrational cycle. The "volume velocity," or product of radial velocity times thickness times circumference, is greatest at the nodal line where contours 430 and 431 cross. The radial pressure distribution corresponding to the phase of contour 430 is illustrated by curve 460, drawn in relation to zero-pressure baseline 470. The lengths of the acceleration/velocity/displacement arrows are related to the slope of contour 460, i.e., to the alternating pressure gradient. Note that the vibration amplitude is greatly exaggerated for illustration. Observe that orifice 126 as labeled in FIG. 1A is located at the radial location of the pressure node in FIG. 4, where curve 460 crosses the zero-amplitude baseline 470. Locating 126 at the pressure node minimizes coupling of vibration through the orifice, which not only reduces noise coupling out of the vibrating chamber, but also minimizes unwanted vibrational couplings that could make the volume-sensing vibration sensitive to external noise and variations in external geometries and compliances, e.g., in cassette 100.

The forming of plate 130 as illustrated in the figures just discussed works particularly well for the purposes of this invention, for establishing a well-behaved vibration mode for sensitive measurement, for giving an appropriately high and linear volume compliance, and for rejecting the effects of external noise and vibration. Though cross-section views tend to underemphasize the relative proportion of formed plate area, it is clear viewing the plate in plan view in FIG. 2 that the formed area between circles 134 and 136 represents significantly more area than the nominally flat area inside circle 134. Under a large upward deflection by volume displacement, as illustrated in FIG. 1C, the curved annulus of metal flattens significantly to accommodate the increased distance from point 134 to point 136, i.e. between the inner and outer radii of the formed bump on the plate. This distance increase is simply the lengthening of a hypotenuse in FIG. 1C as compared to a flat radial baseline as shown in FIG. 1A. If the plate were not formed, the metal would have to stretch radially to accommodate large upward deflections. With the formed bump able to flatten, the in-plane stretch of the metal is substantially reduced, allowing a much greater deflection than could be accomplished with an initially flat plate, without tearing the metal and without having fluid pressure climb too steeply.

An advantage of using a single bump whose section, as viewed in FIG. 1a, is part of a circle, is that this shape is not compliant with respect to pressure change. If the circumference at the radius of 134 were confined against vertical movement, then pressure change under the circular bump between the radii of 134 and 136 would cause virtually no deflection or volume change. Fluid pressure in this outer annular region is quite uniform, as shown in FIG. 4, because the fluid layer in this region is relatively thick and therefore not subject to the large fluid accelerations that take place in the thin layer inside of radius 134 (as observed in the lengths of the radial arrows of FIG. 4). In effect, the vibrating plate is held in place largely by fluid pressure under the curvature-stiffened outer region while most vibrational bending takes place in the central region. Vibrational stress at the outer perimeter attachment, at the radius of 136, is minimal. The "fundamental" or lowest-frequency vibration mode for the plate is largely self-contained and supported by a fluid cushion much more than by mechanical clamping of the edges of the plate.

Furthermore, in its fundamental vibration mode, the center of gravity of the plate and fluid undergoes only minimal vibrational motion, which further decouples vibration sensing from external influence. Considering that at the frequencies used in this device the fluid in layer 128 is virtually incompressible, and since the bottom of layer 128 is a rigid surface, this means that the center of gravity of the fluid in layer 128 undergoes little vertical vibrational motion. When fluid moves up in one region with a thickening of the layer there, a counterbalancing downward fluid motion must take place elsewhere to conserve volume. This balance would be "perfect" for an incompressible fluid under an entirely flat plate undergoing infinitesimal vibrations, while the bump formed in the plate causes the "fixed fluid center of mass" rule to be violated only slightly. As for the center of mass of the plate itself, very little vibration of the plate center of mass would occur for a plate of uniform surface density confined to contain constant volume beneath. The addition of piezoceramic mass 140 at the plate center throws the balance off. The ring at 138 moves in opposite phase to the piezoceramic disk (see FIG. 4, curves 430 and 431), and the mass of this ring is adjusted to obtain a null in center-of-mass vibrational motion. By this balancing, coupling of noise to the exterior is minimized, and simultaneously coupling of external noise into the plate vibration is minimized. This latter effect makes possible a sensor that operates at extremely low power levels and yet remains nearly impervious to the interfering effects of external noise and vibrations. While other plate geometries can meet this noise-immunity goal, the simple geometry shown with a single formed bump of near-circular cross-section and a balance ring performs extremely well and is therefore cited in the specific embodiments taught here.

Figure 5A:
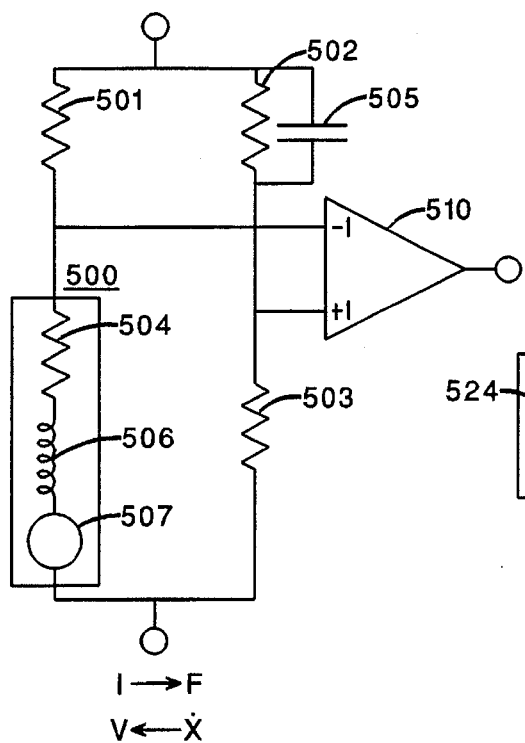
FIG. 5A illustrates schematically a balanced bridge circuit for driving a voice coil transducer and detecting the back-EMF due to coil velocity.
Figure 5B:
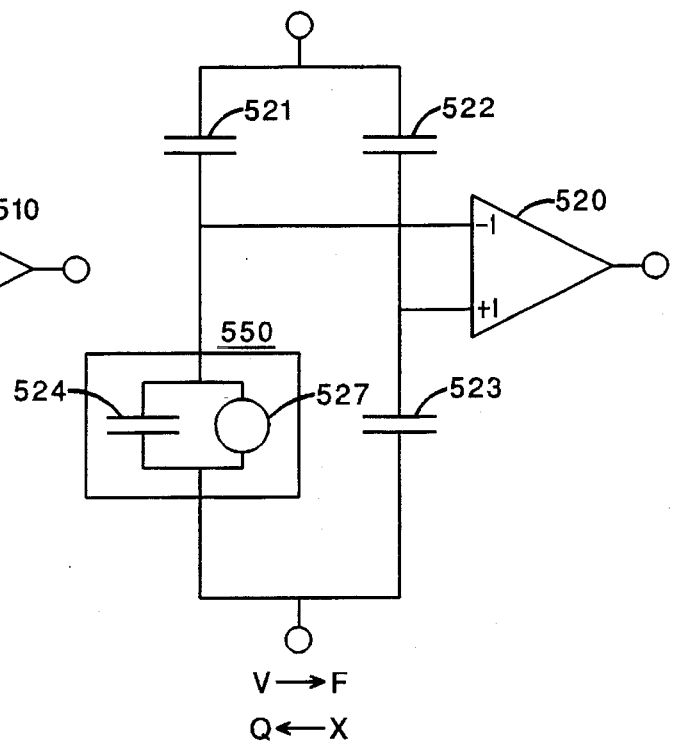
FIG. 5B illustrates schematically a balanced bridge circuit for driving a piezoelectric transducer and detecting the voltage imbalance due to charge displacement arising from strain in the transducer.

FIGS. 5A and 5B illustrate extraction of motion signals from the power lead alone, without an auxiliary sense lead, in the contexts of a voice coil driver (FIG. 5A) and a piezoelectric driver (FIG. 5B). FIG. 5A shows a primarily resistive balanced bridge circuit with output from differential amplifier 510, while FIG. 5B shows a capacitative bridge circuit with output from differential amplifier 520. The electrical and transducer characteristics of the voice coil driver are represented by the components in box 500, namely a winding resistance 504, winding inductance 506, and electromechanical transformer 507, illustrated as a circle that is both a voltage source and a power sink for energy that becomes mechanical. Resistor 504 is in the same ratio to resistor 501 above it as reference resistor 503 is to resistor 502 above it, so that the bridge is nominally balanced at DC. (Because of the high thermal coefficient of copper wire in 504, it is helpful if either resistor 501 or 503 in the bridge has a matching thermal coefficient, to minimize bridge imbalance due to ambient temperature changes, where resistive heating is negligible for the low levels needed for resonance detection.) The effect of inductor 506 is countered by the effect of capacitor 505 in parallel with 502 on the diagonally opposite side of the bridge. The rules for transformer 507 are summarized by the symbols directly below the lower terminal of the bridge. Electric current "I" gives rise to proportionate axial coil force "F". The resulting axial velocity "X-dot" (written as "X" with a dot above) induces electrical voltage "V", which is the so-called electromagnetic back-EMF. By symmetric reciprocity:

$$F = k * I \qquad 1)$$

$$V = k * \dot{X} \qquad 2)$$

where coefficient k is the same in both equations, having equivalent units of newtons/ampere and volts/(meter/second). The purpose of differential amplifier 510 is to extract V, the velocity-induced voltage, where current I is in phase with the current through the left leg of the bridge. At a resonance of the plate, the mechanical load is resistive, and consequently the effective impedance of the transformer circle is resistive. To the extent that the impedance of inductor 506 is small compared to the series resistance on the left side of the bridge, current is in phase with the drive signal from top to bottom of the bridge, while the voltage output of amplifier 510 is in phase with force. Mechanical resonance is defined as the frequency for which force and velocity are in phase and amplitude response is in the vicinity of a local maximum. When the output from amplifier 510 is in phase with the drive voltage, frequency is near the center of resonance, and importantly, volume can be calibrated to this zero-electrical-phase frequency even if that frequency does not precisely match the zero-mechanical-phase frequency of resonance.

In FIG. 5B, capacitors 521, 522, 523, and 524 are the respective counterparts of resistors 501, 502, 503, and 504 of FIG. 5A, forming a capacitive balanced bridge with capacitance 524 of the piezoelectric transducer. As illustrated by the electrical and mechanical symbols below the lower terminal in the figure, piezoelectric transformer 527 transforms applied voltage "V" into force "F", and the resulting effective linear displacement "X" results in a displacement of electric charge "Q".

While voltage "V" and charge "Q" are scalar variables of time, it is not so obvious how to define force "F" and displacement "X" as scalars in relation to the continuous distribution of forces and displacements on the piezoelectric disk. A consistent definition comes from declaring that the product "F*X" equals the energy that is transformed electromechanically. "X" may be defined somewhat arbitrarily in relation to the motion of any reference point on the disk. One appropriate definition is to define "X" as the vibrational axial displacement of the center of disk 140 with respect to the perimeter of that piezoelectric disk. Given a definition, then the definition of force falls out of the energy conservation rule. By these rules of "generalized coordinates" (pioneered by the physicist LaGrange and others), one obtains reciprocity equations 3 and 4, with a single constant "h" appearing in both equations, analogous to reciprocity equations 1 and 2 for the single constant "k":

$$F = h * V \qquad 3)$$

$$Q = h*X \qquad 4)$$

Coefficient h in the two equations has equivalent units of newtons/volt or coulombs/meter. Note that by reversing left and right sides of Eq. 4 and dividing through by "h" one obtains:

$$F*X = V*Q \qquad 5)$$

i.e. mechanical energy (equals force times distance) equals electrical energy (equals voltage times charge). Similarly from Eqs. 1 and 2, one obtains:

$$F*X = V*I \qquad 6)$$

i.e. mechanical power (equals force times velocity) equals electrical power (equals voltage times current). Even though there is energy loss on both the electrical and mechanical sides of these magnetic and piezoelectric transducers, the energy, or power, that is actually transformed in the circle symbol 507 or 527 is conserved in the transformation from one form to another. The conservation of transformed energy leads to the equality of the "k" coefficients in Eqs. 1 and 2, and of the "h" coefficients in Eqs. 3 and 4.

The bridge circuitry of FIG. 5A, along with the transducer and the plate/sensor assembly, are incorporated into SENSOR MODULE 610 of FIG. 6, which is shown with an electrical drive connection 612 labeled "FORCE" since force is nearly proportional to drive voltage, "VELOCITY" output connection 614 from the bridge amp, and connections for a DC power supply and common ground. This module could equally represent the bridge circuitry of FIG. 5B in a piezoelectric context, provided that one add to the bridge amp output a stage of electronic differentiation of the displacement output to approximate velocity phase, at least over the bandwidth where resonance is sought. If a voice coil is equipped with a sense winding, then a velocity signal is obtained with much reduced sensitivity to imbalance and temperature drift, although some small degree of compensation can be provided for electromagnetically induced output voltage from the sense coil not related to coil velocity. Similarly, if a piezoelectric transducer is equipped with a sense metallization, then a position displacement signal is obtained without a balanced bridge. As in the sense winding, some small compensation may be needed for capacitative couplings of drive signal to the sense wire unrelated to mechanical vibration. Bandlimited differentiation then yields a velocity signal.

Considering the variations in motion driving and sensing just described, SENSOR MODULE 610 of FIG. 6 can represent any of a number of electromechanical topologies. One can also incorporate other transduction methods, including hybrids. For example, one can drive magnetically and sense the resulting plate vibration capacitatively, as with a condenser microphone incorporating part of the plate surface as a capacitor surface.

FIG. 6 illustrates how to generate an oscillation at a desired electromechanical resonance. The outer loop is a regenerative feedback loop, with velocity signal 614 being amplified and fed back to generate force in phase with velocity. Maximum regenerative gain will occur at resonance, with a buildup of oscillations. The inner loop on the lower right controls the gain of the outer loop to regulate oscillatory amplitude and maintain low distortion. Specifically, around the outer loop, the velocity signal from 614 is given some gain by "VCA" voltage-controlled amplifier 620, some band-limiting by frequency filter 630, and further power amplification by 640, which drives a transducer or bridge circuit in 610. The band-limiting prevents regenerative feedback at an unwanted harmonic of the multiple frequencies potentially excited by the loop. In the inner loop, the output level from 630 is converted to a filtered amplitude-level signal by "RMS" root-mean-square module 650, which includes an external capacitor-to-ground for setting the effective time averaging period for detected level. The gain-control feedback from 650 to the gain-setting input of VCA 620 is degenerative, i.e. with higher levels causing lower loop gain. This loop settles down to oscillation at a steady amplitude and a frequency determined by one of the resonances of the volume-sensing plate. A frequency count or period count of the resulting oscillation gives a digital output calibratable to volume.

FIG. 7 illustrates a phase-lock-loop approach to the task of converting a resonance into a tracking oscillation. AC excitation arises from Voltage-Controlled Oscillator VCO 720, whose output need not be sinusoidal and might be a triangle wave or even a square wave. The output is applied to the "DRIVE" input of "SENSOR MODULE" 710, which differs from 610. Internal to 710, the "DRIVE" signal may be frequency filtered and amplified before applying the resulting, nearly sinusoidal signal to the transducer. Separate "FORCE" and "VELOCITY" signals are derived from the voltages and currents associated with transducer operation, where the "FORCE" signal emerging at 713 may be greatly phase-shifted from the frequency "DRIVE" signal from the VCO. The relation for correcting VCO frequency is the relative phase of "FORCE" on 713 compared to "VELOCITY" on 714. These two signals are both converted to square waves by comparators 723 and 724, respectively for signals 713 and 714, and the two square waves applied to "PHASE DET" 730, whose output goes through zero as the two input square waves pass through zero relative phase shift. Op amp 740 is wired as an integrator for the jagged output of 730, yielding a low-ripple frequency control signal that sets the frequency output of VCO 720.

An essentially first-order phase-lock-loop circuit of this sort is easier to stabilize than the "usual" second-order phase-lock-loop circuit that is commonly used to lock onto an external frequency signal. In the current circuit, the frequencies entering the two inputs of phase detector 730 are guaranteed to match in the long run, without the kind of slippage of 360-degree phase increments that can happen in a phase-look-loop latching onto an external signal. The frequencies match because they are differing transfer-function phase shifts of the same drive signal. Hence, the loop described here is adjusting frequency in order to correct only phase error with a guaranteed long-term frequency match, an essentially first-order correction, as opposed to correcting frequency to match both an external frequency and also the integral of the frequency error, i.e. phase difference, in an essentially second-order feedback loop.

Note that if a piezoelectric transducer is used with phase-lock-loop tracking of the resonant frequency, one need not approximate a velocity output signal from 710. One can use a "displacement" output phase, "X" rather than "X-dot", seeking quadrature phase of "X" with force "F" rather than zero-phase of "X-dot" with respect to "F". The "PHASE DETECTOR" circuitry for quadrature is then simply a four-quadrant product of the signs (+ or − for logic 1 and 0) of the two inputs, the most common detector found in commercial phase-lock loops. A zero-phase detector requires slightly more complicated "which transition came first?" logic.

It will be obvious without further elaboration that the next step toward the digital world after FIG. 7 involves placing a microprocessor at 720, timing the outputs of 723 and 724 digitally, deriving a cumulative time-difference tally, and synthesizing an output square wave at an appropriately-corrected frequency. The square wave, applied to "DRIVE" at 712, may be filtered in the analog domain, e.g., using a switched-capacitor integrated circuit filter, to yield a good approximation of a sinusoidal output to drive the transducer. This hybrid analog/digital approach to an approximate sinusoid from a square wave is much less demanding of microprocessor power than digital synthesis of a stair-stepped sinusoid approximation using a digital-to-analog converter (DAC).

Of importance is the need to avoid harmonic distortion driving the transducer. If a harmonic frequency, e.g., of a square wave drive, lands on a high-order resonance of plate vibration, it will produce a substantial harmonic distortion component in the motion response output ("VELOCITY" at 714, or possibly displacement "X" substituted at 714 in a piezoelectric implementation). This harmonic will cause an undesirable phase shift in the output of comparator 724, possibly so severe and so frequency sensitive as to cause a non-monotonic relationship between frequency and phase shift, leading to volume ambiguity or frequency jitter or poor reproducibility of volume-versus-frequency calibration.

In the system of either FIG. 6 or FIG. 7, one measures phase characteristics of a transfer function that goes from an electrical measure of FORCE to an electrical measure of VELOCITY, i.e., from 612 to 614 or 713 to 714. This transfer function mirrors a spring plate's mechanical characteristics as modified by the plate's intimate mechanical coupling to a liquid. Hence, one has a transformer of liquid mechanical characteristics into electrical transfer characteristics. The transfer function measurement examples given elsewhere in this specification utilize phase but not amplitude, since phase measurement is time measurement, which is easy and inexpensive. Other forms of transfer function measurement are obvious, e.g., using sampling Analog-Digital data acquisition systems. Suppose that the "DRIVE" signal at 712 of FIG. 7 is an excitation source providing a sufficient number of spectral lines over the desired plate-resonance frequency ranges, e.g., a low-frequency train of narrow pulses, or a random or quasi-random noise signal. Suppose further that "FORCE" and "VELOCITY" outputs 713 and 714 are sampled and digitized over time. Then Fourier transformation of windowed sets of "FORCE" and "VELOCITY" samples, followed by computation of the complex VELOCITY/FORCE ratio in the frequency domain (omitting frequencies where "FORCE" is weak or absent), yields a frequency spectrum of the transfer function, which is interpolated to determine major resonant frequencies and bandwidths, leading to a determination of fluid properties. The key inventions making this possible are the fluid-properties transformer and the methods taught herein for interpreting the transfer function output of the transformer, with some form of excitation and data acquisition needed to bridge from the transformer to computer means that implement the interpreting methods.

Compensation For Fluid Density And Viscosity

As described briefly in the SUMMARY, interpretation of frequencies of more than one resonant mode of the sensor plate can be used to determine density of the working fluid, as well as to detect the presence of air in the transducer. To implement detection of more than one resonance, in FIG. 6 the response of filter 630 can be switched, with maximum response centering in two ranges to give regenerative oscillation at the separate resonances. Smaller switchable perturbations in the phase response of 630 permits determination of phase/frequency slope and implicit damping factors. The circuit of FIG. 7 is readily modified to operate in more than one selectable frequency range, by switching a frequency-determining coefficient in VCO 720. The circuit response will then settle to a resonance within the frequency range accessible to the VCO. Adding a switchable filter in either signal path 713 or 714, to introduce a known small frequency-dependent phase perturbation between the force and velocity signals, will result in a determination of phase/frequency dependence in the vicinity of the tracked resonance. A similar process is feasible for the extension of the FIG. 7 circuit to include a microprocessor substitute for one or more of the functions carried out by 730, 740, and 720.

Each resonant frequency is determined by an effective mode-shape stiffness of the plate and by an inertia, with contributions from fluid mass and plate mass. The mode shape stiffness rises steeply as a function of mode order, from #1 as the "fundamental" mode. The coupled fluid mass decreases with increasing mode order, while plate mass (including a transducer mass contribution) varies relatively little with mode order. The frequency increase with mode order is much steeper than for simple harmonics, e.g., of a string in tension, with the next-higher plate "harmonic" above the fundamental exceeding the fundamental frequency typically in excess of four-to-one. As explained in the SUMMARY, fluid "volume" captured beneath the plate, and the fluid property "specific-volume" as defined to be reciprocal-density, have similar effects on plate-coupled mass and therefore on resonant frequency. If the composition of the working fluid beneath the plate is known, then density will be known fairly accurately in advance, with a possible minor correction for temperature. While moderate temperature changes cause small changes in density, they cause proportionately much larger changes in the viscosity of virtually any working fluid. These viscosity changes in turn alter the damping factors of the plate's resonances, which are readily measured, as described, via determinations of the steepness of frequency variation with the phase angle between force excitation and velocity response in the vicinity of a resonance. For a known working fluid, temperature, and therefore density, are readily inferred from the phase/frequency measurements and the known properties of the working fluid. Hence, full compensation for temperature effects on volume determination is possible from phase/frequency measurements in the vicinity of a single resonance, typically the fundamental resonance.

In certain applications, e.g., when the working fluid under the resonant plate is the same as the fluid whose volume, and possibly other properties, is to be determined, the density and viscosity characteristics of the fluid may not be known in advance. In that case, an independent simultaneous determination of volume, density, and viscosity, is needed to infer any one of the three accurately. If volume measurement is not needed and it is possible to fix the pressure differential across the resonant plate (e.g., by holding pressure to ambient), then density becomes the primary determinant of resonant frequency, with viscosity having a perturbing influence that is readily quantified via phase/frequency slope determination. If all three parameters are needed, i.e. volume, density, and viscosity, then one requires three partly-independent input parameters, e.g. a fundamental resonance frequency, a phase/frequency slope near the fundamental, and a second-mode resonance frequency. Neglecting for the moment the phase/frequency slope and the implicit boundary layer correction for fluid layer thickness, one generally has two resonance frequencies as functions of "volume"— meaning absolute volume captured between the resonant plate and the opposing rigid surface—and "specific-volume"—meaning reciprocal density. The reciprocal frequency-squared of each resonant mode varies roughly as a constant plus the reciprocal of the product of volume times specific-volume. As mentioned earlier, the additive constant is a function of fixed plate and transducer masses relative to a given mode shape. With all harmonics having similar functional dependence on this product of volume times specific-volume, one has no way to solve for the separate terms, volume and specific-volume. Alterations in the shape of the resonant plate with volume changes will redistribute the fluid layer under the plate and redistribute the stiffness of the plate (due to curvature-related nonlinearities), affording some degree of distinction between volume and specific-volume, though the simultaneous solution for volume and density may be mathematically ill-conditioned and of limited practical resolving power.

The design of a second embodiment, described below, deals specifically with this issue. The surface below the resonant plate and defining fluid layer thickness as a function of radius is made non-flat, so that the fluid layer is thinner in certain annular regions and thicker in others. The fluid layer is made thinner in the radial vicinity of the velocity nodal ring for the second-mode resonance, where radial velocity in the first mode is relatively quite high. Hence, this thinner region has a dominant influence on the first-mode frequency and little influence on the second-mode frequency. Thicker regions of the fluid layer effectively control second-mode frequency. With volume changes, there is a larger fractional thickness increase in the thinner region of the fluid layer, compared to the thicker regions controlling second-mode frequency. Hence, the first-mode frequency has a considerably steeper slope with respect to volume than the second-mode frequency, while the slope of frequency-squared with respect to specific-volume is roughly unity for both modes. The ratio between first- and second-mode frequencies therefore becomes a strong indicator of fluid volume alone, with minor influence of specific-volume on this ratio. Hence, a needed degree of functional independence is afforded for the simultaneous solution from two resonance frequencies to determine volume and specific-volume. The relationships described can be quantified through computer simulations of the physical processes involved, or through empirical testing and derivation of empirical calibration functions fitted to the multivariate data. In either case, dependence on the third variable, viscosity, must be quantified, as is now considered.

Viscosity in the fluid in layer 128 gives rise to a boundary layer of fluid whose vibrational acceleration is effectively phase-shifted from in-phase with the pressure gradient (i.e. acceleration limited) to in-phase with radial velocity (i.e. accelerated by velocity-dependent shear forces rather than by pressure gradients arising from bending and unbending of the plate.) As mathematical analysis shows for a fluid boundary layer on a flat surface with a pressure gradient parallel to the surface generating oscillatory flow, there is an effective boundary layer thickness, THK, causing two effects: to reduce the effective cross-section available to flow in-phase with the driving pressure gradient by the amount THK for all wetted surfaces bounding the flow, and to generate a quadrature-phase flow having the same effective thickness THK, with the same velocity amplitude as in the flow external to the boundary layer. In a flat fluid layer of total thickness H and bounded by upper and lower surface, each of which generates a boundary layer of thickness THK, the quadrature-phase flow gives rise to a dissipation factor, DF, in the fluid inertia "inductor", given by:

$$DF=2*THK/(H-2*THK) \qquad 7)$$

This equation is a valid approximation when THK is a small fraction of H, i.e. at dissipation factors much less than unity. The fluid layer thickness H' that is left over as fluid "inductor" is given by:

$$H'=H-2*THK \qquad 8)$$

If resonance is defined as the frequency at which the driving force is in-phase with the responsive velocity, then the fluid layer thickness that effectively determines resonance frequency is given by H'. Given a measured resonance frequency, therefore, H' comes out of the system calibration. The dissipation factor is related to the resonance phase-versus-frequency curve as follows:

$$DF=d(PHI)/d(LN(OMEGA)) \text{ at resonance}, \qquad 9)$$

i.e., DF is the slope of phase angle PHI plotted against the natural logarithm of frequency OMEGA, the slope measured at PHI=0, i.e. with velocity in-phase with force at resonance. Since the shape of the curve of PHI versus LN(OMEGA) is consistent under different conditions, it is possible to determine DF from a finite increment in OMEGA and PHI, rather than a tangent slope. This can be accomplished in the circuit of FIG. 6 by altering the phase-shift across filter 630 by a relatively small amount, not enough to shift the system to a different resonance, but rather enough to move the system moderately in relation to center-resonance. When the phase/frequency curve of 630 is known for both unperturbed and perturbed settings, enough information is present from a pair of frequencies near a given resonance to determine the zero-phase frequency, OMEGA-O, and the dissipation factor, DF. From OMEGA-O one solves for effective H', and hence for volume (given an effective area associated with H'). From DF and H', using Eqs. 7 and 8, one solves for THK, leading immediately to a corrected fluid layer thickness H and a corrected volume estimate. Further incorporating the dual-mode determination of fluid density, one obtains separate figures for fluid volume, density, and viscosity.

Another performance issue is bubbles entrapped in the vibrating fluid layer. Bubbles will obviously alter the resonant dynamics of the plate. This alteration will be seen as an apparent shift in the density and viscosity of the vibrating fluid. If the composition of the vibrating fluid is known, as in the case for the preferred embodiment where the vibrating fluid is permanently in-place, like brake fluid, isolated from the fluid to be measured in the cassette, then any inconsistent apparent density or density/viscosity relationship is a warning indicator. Even a relatively small bubble will cause the apparent density to fall outside the possible density range for the working fluid. While a very small bubble could yield an apparent density consistent with a credible temperature, the apparent viscosity will not in general be consistent with the temperature implied by apparent density. Frequency measurement at one or more additional harmonics will resolve any remaining ambiguity. Thus, the system detects "air in the brake lines" reliably and can call for corrective purging of air.

Although this invention has been described as a volume-measurement device, it is clear that the same mechanism can be used to measure density and viscosity in fluids of unknown composition, provided that those fluids are allowed to interact directly with the vibrating plate. The second embodiment of the invention accomplishes this.

DESCRIPTION OF A SECOND EMBODIMENT

A preferred embodiment of the invention has been described using separate fluids for delivery, in a cassette, and for volume displacement sensing, in the sensor module. While for volume measurement alone it may be advantageous to have a separate liquid of known density contacting the resonant plate, considerations of mechanical simplicity may favor a single-fluid design employing the deliverable fluid directly in the resonance measurement. In the event that the fluid density may be unknown, provision is needed for measuring and computing density and volume separately, either to disentangle interacting measurement effects to yield an accurate volume measurement, or to yield density as a useful parameter measurement in itself. In either case, simultaneous viscosity determination can refine density/volume determinations.

Comparing the embodiment illustrated in FIGS. 8A and B with respective FIGS. 1A and B, it is seen in the transformation of transducer module 120 into 820 that rigid barrier 150 is eliminated, with surface 810 of mating cassette 800 taking over the function of the upper surface of barrier 150, capturing fluid below the plate and setting up conditions for the volume- and property-measuring resonance. Elastomer plug 122 is replaced functionally by elastomer fill layer 822, which fills in the bumps and voids of the formed plate surface to provide a smooth convex mating surface contour for the cassette. Plate 830 is shown flipped upside down compared to analogous plate 130, this being a convenience for recessing the coupling screw head in relation to the formed surfaces of the plate. The drive/sense function is electromagnetic, a variation on FIG. 3 but with moving magnet instead of moving coil. Cassette membrane 808 is comparable to 108, with cavity 806 comparable to both cavities 106 and 128, the latter being the resonant cavity of FIG. 1A. There are inlet and outlet ports 802 and 804, like 102 and 104 except that the corresponding narrow fluid channels 825 and 827 function as large-value fluid inductors to block vibrational fluid flow between cavity 806 and external fluid-handling apparatus. The fluid inductances of these channels (equaling fluid density times length divided by cross-section area) must be sufficient to prevent impedance variability in the fluid environment from affecting volume determinations based on frequency.

Figure 8A:
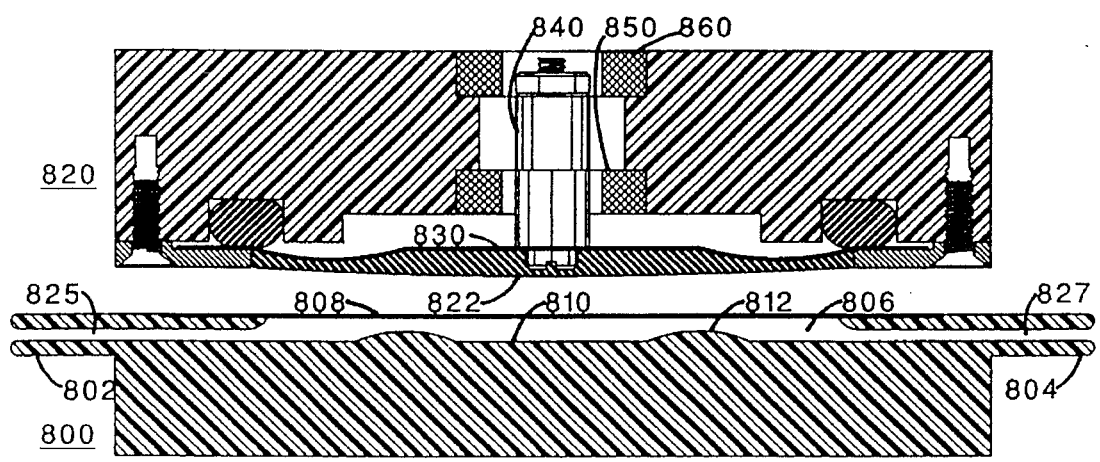
FIG. 8A illustrates, in a second embodiment, the transducer module and the fluid cassette, as shown separated, wherein transducer vibrations couple directly into the cassette fluid, and wherein volume, density, and viscosity are all measured.
Figure 8B:
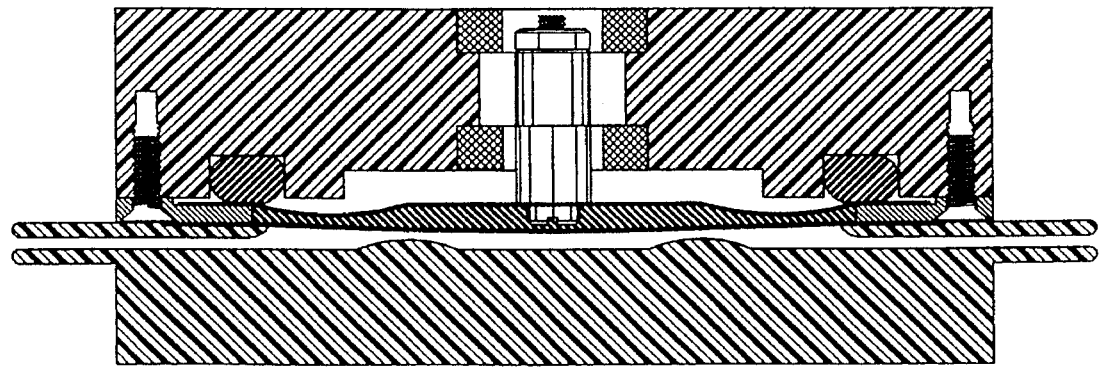
FIG. 8B provides the same illustration as that of FIG. 8A except that the transducer module and the cassette are joined.

Illustrating a variation on the electromagnetic transducer theme of FIG. 3, in FIGS. 8A and 8B a magnet moves with respect to fixed coils. A screw penetrating the center of plate 830 extends on the side away from the fluid interface, passes through a standoff cylinder, through cylindrical bead-shaped magnet 840, and thence through a retaining nut. Coaxial with 840 and offset in their axial centers are sense coil 850, offset toward the fluid interface with respect to the magnet center, and excitation coil 860, offset away from the fluid interface. The coils could be interchanged in excitation and sense functions, or for symmetry, both coils could include separate excitation and sense windings.

A final modification is made in surface 810 to provide for discrimination between change in volume and change in specific-volume, i.e. reciprocal density, as discussed earlier. The bump labeled on the right as 812 and seen mirrored across the plate center is a sectional view of a rounded annular ridge in surface 810, causing an annular region of reduced thickness in fluid layer 806. This reduced thickness region is located in the vicinity of peak radial oscillatory flow for the fundamental mode of plate vibration, and the vicinity of a nodal ring in flow for the next-higher frequency mode. Given an increase in fluid volume beneath the plate and a corresponding rise in the plate surface, the fluid layer above bump 812 will experience a larger fractional increase in thickness than the thicker regions of the fluid layer that are primary determinants of the second-mode vibration frequency. The ratio of mode frequencies is therefore comparatively sensitive to volume change and comparatively insensitive to specific-volume change. Hence, as discussed earlier, separate frequency measurements for the two modes may be combined with a non-singular system of equations to solve independently for volume and density. Phase-shifted frequency measurements refine this solution while adding viscosity to the list of determined variables.

Other geometries can clearly be employed to resolve density and volume as separable measurements, e.g., circular ridge bumps matched to the flow antinodes of a second-mode vibration, causing a slightly more pronounced volume/frequency sensitivity in the second-mode than in the fundamental (though the distinction may be weaker in this direction, since the fundamental mode does not exhibit any nodal ring for locating a bump.) An alternative geometry is shown in the referenced patent application of Joseph B. Seale entitled "A RESONANT SYSTEM TO PUMP LIQUIDS, MEASURE VOLUME, AND DETECT BUBBLES," Ser. No. 08/258,327, filed Jun. 10, 1994. As illustrated in FIG. 3 of that application, fluid layer 312 is captured both below resonant plate 310 and to the outside of a cylindrical plug 301 extending down from the middle of 310, yielding a thin fluid washer joined on its inside to a thin fluid cylinder extending down. Volume changes alter the thickness and inertial impedance of the washer-shaped fluid region while leaving the thickness of the cylinder region unaltered and the impedance only slightly altered (due to a change in effective length of the cylinder). Specific-volume changes in the fluid alter the inertial impedances of the two regions in equal proportions. Since the two lowest resonant modes depend in different proportions on the inertia contribution from the cylinder region, their frequencies are affected differently by volume change and about the same by specific-volume change, yielding a non-singular simultaneous solution for volume and density.

From the above discussions it will be seen that many mechanical and geometric variations, many electromechanical transducer interfaces, many electronic and digital interface designs, and many algorithmic variations in system control and signal interpretation, can be mixed and matched to obtain successful measurements of fluid volume displacement, density, and viscosity, provided that these system components are organized according to the invention taught by precept and example in the above disclosure and described in the following claims.

I claim:

1. A system for transforming a variable confined liquid volume into a variable electrical frequency response indicative of said liquid volume, said system comprising:

a. a housing including a cavity for receiving a liquid having a volume to be measured;

b. a deformable spring plate forming a part of a boundary of said cavity and confining vibrational movement of mass of said liquid, wherein a frequency of a vibration mode of said spring plate is sensitive to variations in inertia as a function of geometric variations of said confining; and c. means coupled to said spring plate, said means for transforming characteristics of said vibration mode into electrical response characteristics indicative of said frequency of said vibration mode.

2. The system as claimed in claim 1 further comprising means to analyze said electrical response characteristics to determine an electrical resonant frequency indicative of said frequency of said vibration mode of said spring plate.

3. The system as claimed in claim 2 wherein said means to analyze said electrical response characteristics further determines a damping factor associated with said electrical resonant frequency, and wherein said electrical resonant frequency and said damping factor are used to compute said volume to be measured, compensating for variations in a viscosity of said liquid.

4. The system as claimed in claim 2 wherein said means to analyze said electrical response characteristics further determines a secondary electrical resonant frequency indicative of a frequency of a second vibration mode of said spring plate, and wherein said electrical resonant frequency and said secondary electrical resonant frequency are used to compute said volume to be measured, compensating for variations in a density of said liquid.

5. The system as claimed in claim 4 further comprising:
   a. means to determine a magnitude of compensation required for said variations in said density of said liquid;
   b. means to determine a maximum of said magnitude of compensation consistent with said variations; and
   c. means to detect when said magnitude of compensation exceeds said maximum, indicating a probability of bubbles in said liquid.

6. The system as claimed in claim 2 wherein said means to analyze said electrical response characteristics further determines a secondary electrical resonant frequency indicative of a frequency of a second vibration mode of said spring plate, said means to analyze said electrical response characteristics comprising:
   a. means to determine a normal range of variation of said electrical resonant frequency and said secondary electrical resonant frequency; and
   b. means to determine whether said electrical resonant frequency and said secondary electrical resonant frequency fall outside said normal range, indicative of a probability of bubbles present in said liquid.

7. The system as claimed in claim 1 further comprising means for transforming said electrical response characteristics into multiple amplitude ratios corresponding to multiple frequencies of said electrical response characteristics.

8. The system as claimed in claim 7 wherein said multiple amplitude ratios are used to compute one or more of said mechanical characteristics of said deliverable liquid selected from the group consisting of volume displacement, density, and viscosity.

9. The system as claimed in claim 1 further comprising response measurement means coupled to said means for transforming characteristics, wherein said response measurement means generates one or more frequency response signals from said electrical response characteristics.

10. The system as claimed in claim 9 wherein said means for transforming said characteristics includes a transducer and said response measurement means includes an impedance bridge circuit.

11. The system as claimed in claim 9 wherein said response measurement means includes a regenerative feedback oscillator.

12. The system as claimed in claim 9 wherein said response measurement means includes a phase-lock-loop oscillator.

13. The system as claimed in claim 1 further comprising:
   a. means to infer said inertia from said frequency of said vibration mode of said spring plate;
   b. means to infer a thickness of said confined liquid volume from said inertia and a density of said liquid; and
   c. means to infer said volume of said liquid from said thickness.

14. The system as claimed in claim 13 further comprising a working liquid coupling said liquid to said spring plate.

15. A system for transforming a variable confined liquid volume in a disposable cassette into a variable electrical frequency response indicative of said liquid volume, said system comprising:
   a. a disposable housing including a cavity for receiving a liquid having a volume to be measured, and a deformable membrane for isolating said liquid in said cavity;
   b. a measurement device having a deformable spring plate coupled to said cavity, wherein a frequency of a vibration mode of said spring plate is sensitive to variations in inertia of said liquid; and
   c. means coupled to said spring plate, said means for transforming characteristics of said vibration mode into electrical response characteristics indicative of said frequency of said vibration mode.

16. The system as claimed in claim 15 further comprising means to analyze said electrical response characteristics to determine an electrical resonant frequency indicative of said frequency of vibration of said spring plate.

17. The system as claimed in claim 16 wherein said means to analyze said electrical response characteristics further determines a damping factor associated with said electrical resonant frequency, and wherein said electrical resonant frequency and said damping factor are used to compute said volume to be measured, compensating for variations in a viscosity of said liquid.

18. The system as claimed in claim 16 wherein said means to analyze said electrical response characteristics further determines a secondary electrical resonant frequency indicative of a frequency of a second vibration mode of said spring plate, and wherein said electrical resonant frequency and said secondary electrical resonant frequency are used to compute said volume to be measured, compensating for variations in a density of said liquid.

19. The system as claimed in claim 16 wherein said means to analyze said electrical response characteristics further determines a secondary electrical resonant frequency indicative of a frequency of a second vibration mode of said spring plate, said means to analyze said electrical response characteristics comprising:
   a. means to determine a normal range of variation of said electrical resonant frequency and said secondary electrical resonant frequency; and
   b. means to determine whether said electrical resonant frequency and said secondary electrical resonant frequency fall outside said normal range, indicative of a probability of bubbles present in said liquid.

20. The system as claimed in claim 15 wherein said means for transforming characteristics includes excitation means for exciting said spring plate.

21. The system as claimed in claim 20 wherein said means for transforming characteristics includes sensing means for sensing said characteristics of said spring plate.

22. The system as claimed in claim 21 wherein said excitation means is a piezoelectric transducer.

23. The system as claimed in claim 22 wherein said sensing means is selected from the group consisting of a piezoelectric transducer, a coil-and-magnet transducer, an optical sensor, a capacitance sensor, and a resistance strain gauge sensor.

24. The system as claimed in claim 21 wherein said excitation means is a coil-and-magnet transducer.

25. The system as claimed in claim 24 wherein said sensing means is selected from the group consisting of a piezoelectric transducer, a coil-and-magnet transducer, an optical sensor, a capacitance sensor, and a resistance strain gauge sensor.

26. The system as claimed in claim 21 wherein said excitation means is a capacitance transducer.

27. The system as claimed in claim 26 wherein said sensing means is selected from the group consisting of a piezoelectric transducer, a coil-and-magnet transducer, an optical sensor, a capacitance sensor, and a resistance strain gauge sensor.

28. A method for transforming a variable confined liquid volume into a variable electrical response indicative of said volume, said method comprising the steps of:

a. confining within a cavity of a housing vibrational movement of mass of a liquid having a volume to be measured;

b. providing means for sensing variations in inertia as a function of geometric variations of said confining, wherein said means for sensing includes a deformable spring plate coupled to said liquid and having a vibration mode associated with a frequency; and c. transforming characteristics of said vibration mode into electrical response characteristics indicative of said frequency of said vibration mode.

29. The method as claimed in claim 28 further comprising the step of analyzing said electrical response characteristics to determine an electrical resonant frequency indicative of said frequency of said vibration mode of said spring plate.

30. The method as claimed in claim 29 further comprising the step of determining a damping factor associated with said electrical resonant frequency.

31. The method as claimed in claim 29 further comprising the step of determining a secondary electrical resonant frequency indicative of a frequency of a second mode of vibration of said spring plate.

32. The method as claimed in claim 29 further comprising the steps of:

a. determining a secondary electrical resonant frequency indicative of a frequency of a second mode of vibration of said spring plate;

b. determining a normal range of variation of said electrical resonant frequency and said secondary electrical resonant frequency; and c. determining whether said electrical resonant frequency and said secondary resonant frequency fall outside said normal range.

33. The method as claimed in claim 28 further comprising the step of transforming said electrical response characteristics into multiple amplitude ratios corresponding to multiple frequencies of said electrical response characteristics.

34. The method as claimed in claim 33 further comprising the step of converting said multiple amplitude ratios and said corresponding multiple frequencies into one or more of said mechanical characteristics selected from the group consisting of displacement, density, and viscosity.

35. The method as claimed in claim 28 further comprising the step of physically isolating said liquid from said spring plate by means of an elastic membrane.

36. The method as claimed in claim 28 wherein the step of transforming characteristics of said spring plate into electrical response characteristics includes affixing transducer means to said spring plate.

37. The method as claimed in claim 36 wherein said transducer means is a piezoelectric transducer having an electrically isolated area for excitation and an electrically isolated area for response detection.

38. A system for transforming a variable confined liquid volume into a variable electrical frequency response indicative of said volume, said system comprising:

a. a resonance disk mechanically coupled to and deflectable by a liquid having a volume to be measured, wherein said disk provides a confining of vibrational movement of mass of said liquid, and wherein a frequency of a vibration mode of said disk varies with inertia as a function of geometric variations of said confining; and b. transducer means coupled to said disk for obtaining and transforming characteristics of said vibration mode of said disk into electrical response characteristics.

39. The system as claimed in claim 38 further comprising an elastic membrane located between said liquid and said disk.

40. The system as claimed in claim 38 further comprising an elastic barrier positioned between said liquid and said disk, wherein a space formed between said elastic barrier and said disk includes a working liquid.

41. The system as claimed in claim 40 with said space containing said working liquid further comprising a first chamber proximal to said disk and a second chamber proximal to said elastic barrier.

42. The system as claimed in claim 41 further comprising an orifice connecting said first chamber to said second chamber.

43. The system as claimed in claim 42 wherein said disk includes a pressure node and said orifice is aligned with said pressure node.

44. The system as claimed in claim 38 wherein said disk includes a curved annulus concentric to the center of said disk.

45. The system as claimed in claim 44 wherein the surface area of said curved annulus is greater than the surface area of a portion of said disk bounded by said curved annulus.

46. The system as claimed in claim 38 wherein said disk includes a plurality of curved annuli concentric to the center of said disk.

47. The system as claimed in claim 46 wherein the total surface area of said plurality of curved annuli is greater than the surface area of a portion of said disk bounded by an innermost curved annulus of said plurality of curved annuli.

* * * * *